United States Patent [19]

Tarrone

[11] 4,101,979
[45] Jul. 25, 1978

[54] WELDING MASK WITH AUTOMATIC OBSCURING OF THE VISUAL FIELD

[76] Inventor: Eugenio Tarrone, Via Antonio Cecchi 3, I-10152 Torino, Italy

[21] Appl. No.: 740,209

[22] Filed: Nov. 9, 1976

[30] Foreign Application Priority Data

Dec. 16, 1975 [IT] Italy .............................. 70094 A/75
Nov. 5, 1976 [IT] Italy .............................. 69641 A/76

[51] Int. Cl.² .............................................. A61F 9/06
[52] U.S. Cl. ................................................... 2/8
[58] Field of Search ................... 2/8, 10, 432, 11, 9

[56] References Cited

U.S. PATENT DOCUMENTS

| | | | |
|---|---|---|---|
| 2,171,052 | 8/1939 | Tatter | 2/8 |
| 2,384,517 | 9/1945 | Zimmerman et al. | 2/8 |
| 2,693,597 | 11/1954 | Horlbeck | 2/8 |
| 2,761,046 | 8/1956 | Herrick | 2/8 X |
| 3,838,466 | 10/1974 | Poirier | 2/10 |

FOREIGN PATENT DOCUMENTS

| | | | |
|---|---|---|---|
| 1,036,837 | 4/1953 | France | 2/8 |
| 2,428,301 | 1/1976 | Fed. Rep. of Germany | 2/8 |

*Primary Examiner*—Werner H. Schroeder
*Assistant Examiner*—Peter Nerbun
*Attorney, Agent, or Firm*—Young & Thompson

[57] ABSTRACT

A mask for carrying out electric arc welding by protecting the operator's eyes against both the glare and the ultraviolet rays during operation and reducing to a minimum the period of lack of visibility, which is embodied by an opaque shell with a vision window normally not obscured but provided with an oscurator means which is rendered operative upon flowing of electric current through an actuation apparatus connected to the electric welding circuit.

4 Claims, 7 Drawing Figures

WELDING MASK WITH AUTOMATIC OBSCURING OF THE VISUAL FIELD

BACKGROUND OF THE INVENTION

The present invention relates to a protection mask for those who carry out electric arc welding, which mask automatically obscures the field of vision when the electric arc is lighted.

As is well-known, the electric arc emits an intense light having a high content of ultraviolet rays, and the eyes of the people carrying out the welding have to be protected against both the glare and the effect of the ultraviolet rays. At present time this is achieved by means of masks provided with a window of obscured glass which are manipulated manually by placing them before the face prior to welding. Such manipulation seriously hinders the work because of the total absence of visibility through the obscured glass between the moment in which the mask has been placed before the face and the moment in which the arc is lighted.

To try to find a remedy for this disadvantage, masks have been proposed in which the obscured glass may be manually displaced out of the visual field; this facilitates the welding operation, but does not allow one to avoid a period of lack of visibility and the possibility of injuries to the eyes in the case of delay in operating the obscuration. In any case, however, the fact that the operator must hold the mask as well as the welding gun at the same time and trail along the electric feeding cable constitutes a heavy hindrance and gives rise to dangers when the welding has to be carried out in not very accessible places, such as for instance wells, stairs and the like.

BRIEF SUMMARY OF THE INVENTION

The object of the present invention is to provide a mask which may be put on permanently, for example by connecting it to a helmet or support, without hindering the normal visibility, and which obscures automatically the visual field in those periods of time only, in which the electric arc is lighted. In this way, the free visibility is maintained up to the moment in which the arc is lighted, whereupon the visibility remains ensured even through the obscured glass, and the normal visibility is restored as soon as the arc is extinguished. Moreover, the disadvantages and dangers inherent in the necessity to hold the mask are avoided and it is also possible to avoid having to hold in one's hand the heavy cable of the welding machine, especially during the displacements thereof.

According to the present invention, the above object is achieved by means of an opaque mask provided with means for supporting it permanently before the operator's face and with a normally clear window whose field can be obscured by an absorption means controlled, directly or indirectly, by the welding current.

BRIEF DESCRIPTION OF THE DRAWINGS

One embodiment of the invention will now be described in detail herebelow with reference to the accompanying drawings, in which.

DETAILED DESCRIPTION OF THE PREFERRED EMBODIMENTS

Figure 1:
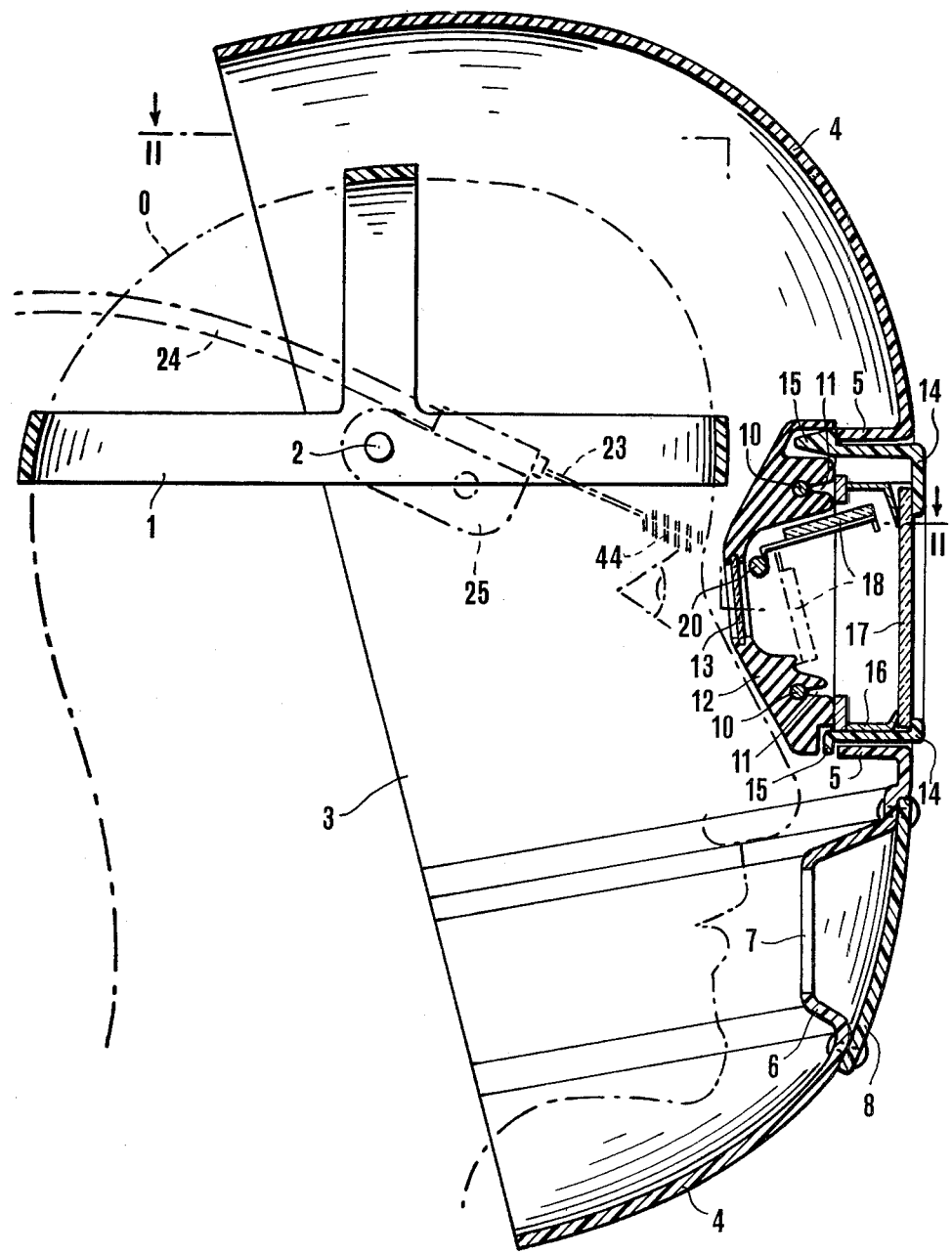
FIG. 1 is a side elevational cross-sectional view along line I—I of FIG. 2, showing the welding mask in its put-on condition.

The welding mask according to the embodiment shown is formed by a shell, which may preferably be made of moulded plastic material and which comprises side elements 3 connected, by pivoting means 2, to a support cross 1 applicable to the operator's head indicated by dashed line at 0. This cross will not be described in detail, as it is well-known per se and can be found on the market. The shell of the mask is completed, between the side elements 3, by a central element 4 which extends before the operator's face and partly over it and below the chin, when the mask is in its operative position shown. However, thanks to its being pivoted at 2, the mask can be lifted and turned over the operator's head, without removing the cross 1, during the time intervals between the welding operations, thus leaving completely free the visual field of the operator.

At the level of the operator's eyes (when the mask is in its operative position), the shell of the mask is provided with a vision window limited by rims 5. At the level of the operator's mouth, the shell has also a channel-like recessing 6, extending towards the rear end, having centrally an aperture 7 and covered externally by a plate 8. The aperture 7 is located in such a manner as to receive operator's expiration, both from the nose and from the mouth, so that the air expired is conveyed outwards through the channel 6, thereby changing the air contained in the inner space of the mask.

Applied onto the side rims 5 of the vision window are support brackets 9, preferably made of metal, which support a pair of transverse bars 10 having hooked thereon, by means of profiled slots 11, a body 12 made of rubber or the like, provided with an almost rectangular window having restrained therein an inner glass 13. Preferably, this glass is treated by means of known processes in order to render it protective against infrared radiations.

Inserted from the outside into the vision window, between the rims which delimit the latter, is a frame of plastic material 14 which hooks itself in position by means of hooks 15 and retains in its interior, by means of a retainer member 16, an outer glass 17. Preferably, this latter glass is of a type, for instance containing iron ions, which is adapted to absorb the ultraviolet radiations. In this way, the operator is permanently protected (even during the periods of time which are not specifically reserved to the welding operations) both against the infrared radiations (thanks to the inner glass 13) and against ultraviolet radiations (thanks to the outer glass 17), without any hindrance of the vision. Thus, he cannot be injured by radiations emitted from adjacent working stations in which welding operations are carried out.

Figure 2:
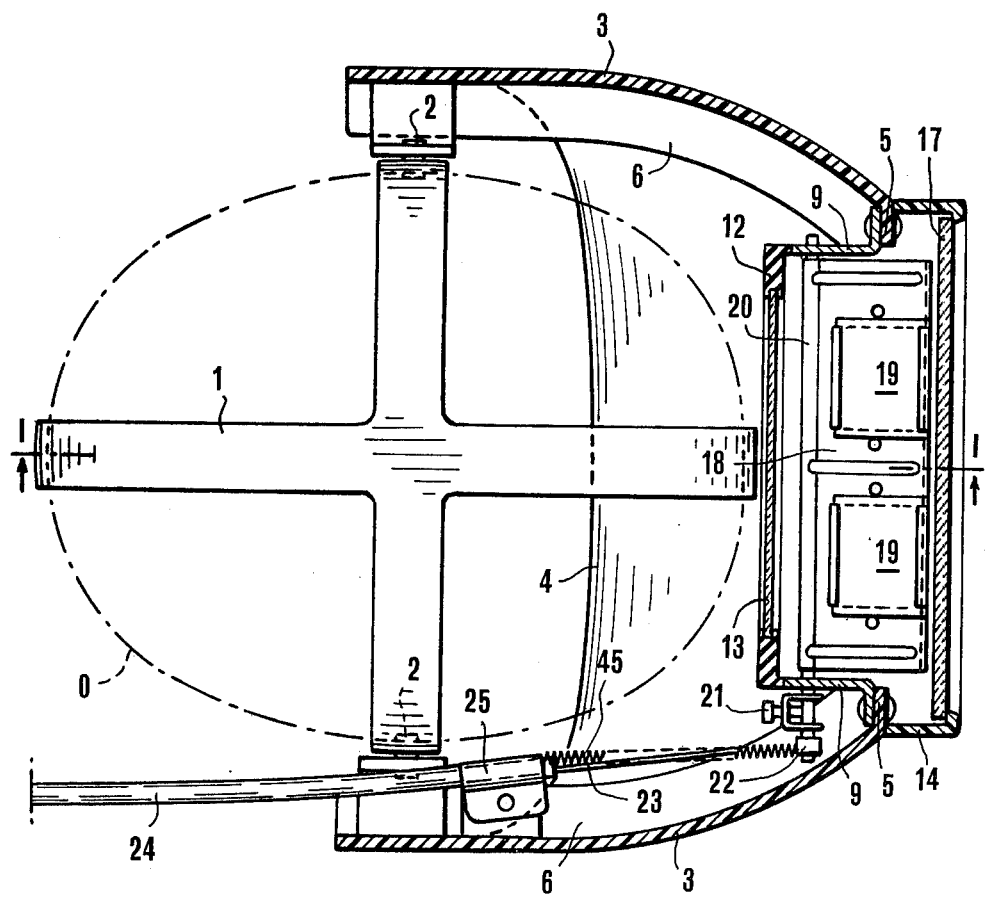
FIG. 2 is a top cross-sectional view thereof, taken along line II—II of FIG. 1.

Housed in the closed chamber defined by rubber body 12 and frame 14 between the inner glass 13 and the outer glass 17 is a mobile frame 18 rigidly connected to a shaft 20 pivotally supported by the brackets 9, so that the frame 18 can move between a rest position shown by continuous lines in FIGS. 1 and 2 and an operative position shown by dashed lines in FIG. 1. The frame 18 carries, mounted on windows, a pair of small glasses 19, each of which corresponds to the visual field of one eye of the operator, when the frame 18 is in its operative position. The glasses 19 are of a type having a high degree of absorption of the rays of light, i.e. of the type which is usually employed for welding spectacles and masks. However, since the ultraviolet rays are absorbed already by the outer glass 17, said glasses 19 could also be made of a lighter material, as for instance a suitable plastic material, adapted to absorb the rays of light, but not the ultraviolet rays.

Keyed on an outer end of the shaft 20 by means of an adjusting member 21 is a short lever 22 having connected thereto an end of a flexible cable 23 whose sheath 24 is anchored in a suppport 25 rigidly connected to the side element 3 of the mask. These latter parts are shown by dashed lines in FIG. 1 because they are located in the mask portion which is removed by drawing the cross-section. Also hooked onto the lever 22 is a return spring 45, whose opposite end as well is fixed to the support 25. This return spring is disposed in such a way as to displace the frame 18, by means of the lever 22 and the shaft 20, towards the rest position, while cable 23 is connected in such a way that a traction exerted on it will move frame 18 towards the operative position.

Figure 3:
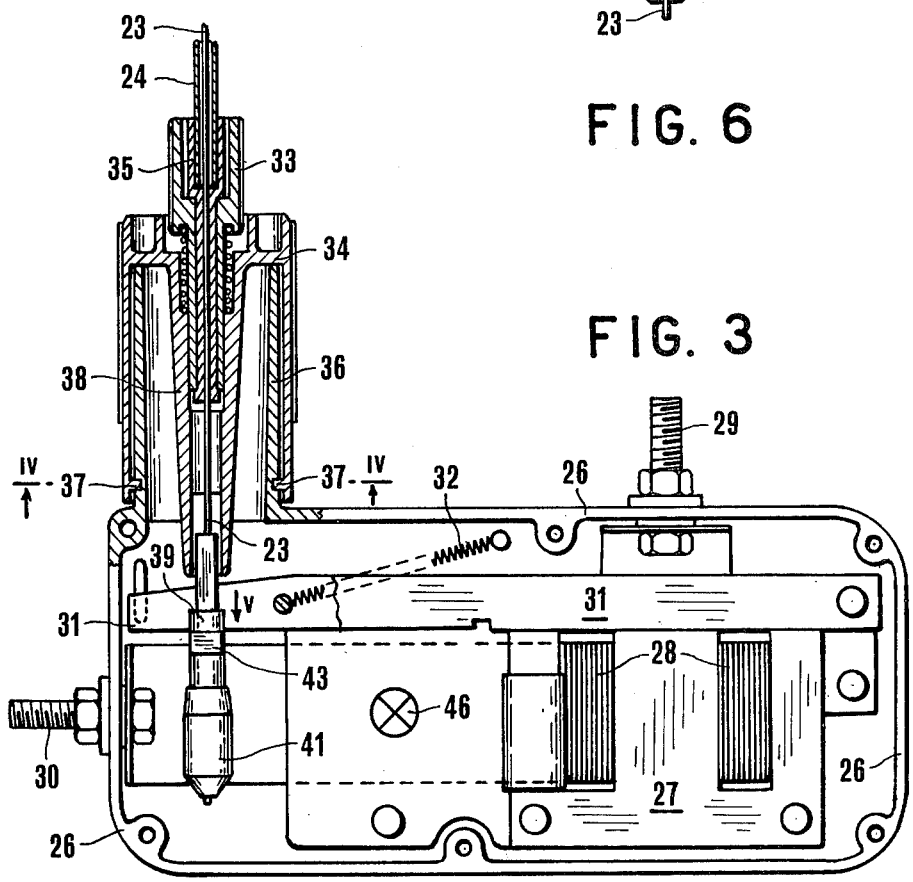
FIG. 3 is a cross-sectional view of a mask actuating device.

The opposite ends of the flexible cable 23 and of the sheath 24 are connected to an actuating device, shown in FIG. 3. This device comprises a housing 26, which may for example be connected to the operator's belt or may be located at a fixed point in the vicinity of the operator's working place. Housing 26 contains an electromagnet 27 whose winding 28 is connected to two connections 29 and 30 protruding from the housing 26. The electromagnet 27 acts on a mobile keeper 31 which normally is maintained in a rest position by a return spring 32, but is shown in FIG. 3 as attracted by the electromagnet. Keeper 31 in turn acts on the end of the flexible cable 23 applying on it a traction, when the electromagnet 27 is excited.

The sheath 24 of the cable 23 rests on a stretcher 33 screwed into a ring nut 34, which stretcher serves for setting up the actuating device. Interposed between the sheath 24 and the stretcher 33 is a freely rotatable bush 35 which prevents sheath 24 from being accidentally twisted. The ring nut 34 is mounted on a neck 36 of the housing 26 and is fixed thereon by means of a bayonet joint engageable by a 90° rotation of the ring nut. Furthermore, the ring nut 34 extends internally with a neck 38, into the end of which there is inserted a slide 39, movable axially but not rotatable, coupled, by means of a preloaded spring 40, with a head 41 on which the end of the flexible cable 23 is anchored by means of a setscrew 42. Slide 39 is provided with shoulders 43, by means of which it may receive the thrust of the movable anchor 31, when it is in the operative position shown, but the slide 39 disengages from the anchor 31 when it is rotated by 90°. Therefore, disengagement of the bayonet joint 37 produces also the disengagement of the slide 39 from the anchor 31, and thus allows one to detach the ring nut 34 with all the parts connected to the cable 23, from the housing 26; moreover, owing to the arrangement, the coupling can take place in the correct position only.

Preferably, the neck 36 of the housing 26, and the ring nut 34, are sufficiently long to prevent any contact between the head 41 and the anchor 31 as long as the ring nut 34 is not mounted correctly onto the neck 36, whereby the insertion of the parts into one another can take place in the correct position only.

The connections 29 and 30 are inserted into the circuit of the welding machine used by the operator. Depending on the applications it may be suitable to insert such connections (and, consequently, the winding 28 of the electromagnet 27) in series with the cable which feeds the welding electrodes, or in parallel; obviously, the winding must be sized suitably. In any case, the electromagnet is excited during the periods of time in which the welding current is flowing, and remains de-energized when said current does not flow.

Therefore, when the operator, after having put on the mask, is on the point of carrying out a welding, he has a non obscured vision, because the frame 18 with the obscured glasses 19 is in a lifted rest position. As soon as, after the electrode has been brought into contact, the current begins flowing, the electromagnet 27 attracts the anchor 31 which actuates the slide 39 and, by means of the spring 40 (which prevents excessive stresses in case of high currents), pulls the cable 23, thereby lowering the frame 18 and obscuring the visual field of the operator. As soon as the welding electrode is detached, thereby switching off the current, the whole apparatus returns to the rest position and the operator immediately obtains again unobscured vision.

The preloaded spring, intended to prevent overloads, may generally be mounted in any point of the kinematic system, and for example also at 44, between the cable 23 and the lever 22, as shown partially and by dash lines in FIG. 1.

Figure 6:
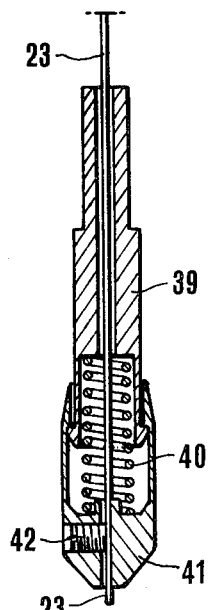

In FIG. 6 there is shown in detail, on an enlarged scale, a protection device having a preloaded compression spring. In this device, the head 41 having anchored thereon the flexible cable 23 by means of the setscrew 42, is attached in such a way as to be axially slidable along a limited path with respect to the slide 39, and the compression spring 40 is lodged in the compressed condition between said parts. It yields only in case of a stress higher than its preloading.

Figure 7:
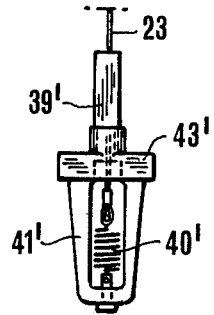
FIGS. 6 and 7 are views showing on the enlarged scale two embodiments of a preloaded spring device serving to prevent overloads.
Figure 4:
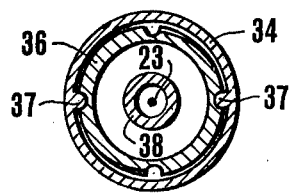
FIGS. 4 and 5 show details of a device for the connection of a flexible transmission cable.
Figure 5:
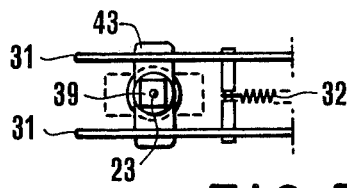

In the variant shown in FIG. 7, the slide 39' extends to form by itself the head 41' in the shape of a bracket, on which there is anchored the preloaded spring 40', which in this case is an extension spring, on which there is in turn anchored the flexible cable 23.

In any case, at some point on the cable 23 or on the elements connected to it, there is disposed a rotatable joint intended to prevent twisting of the cable.

In the cases in which the winding 28 has to be inserted in parallel to the welding circuit, for example in the case of continuous feed welding, it is advantageous to insert an incandescent lamp (diagrammatically shown at 46 in FIG. 3) in series with the winding, in order to allow the initial passage of a high actuating current and to successively limit the consumption, owing to the known characteristic of variation of the electric resistance of an incandescence lamp.

Obviously, instead of a lamp also other components or circuits may be used in view of obtaining this effect.

In accordance with possible modifications, the obscuration of the field could also be obtained by the cooperation of two crossing polarizing filters, one of which is fixed and the other is movable, or by means of an element whose transparency varies as a result of the application of a field or of an electric current.

Having thus described my invention, what I claim is:

1. In a welding mask for carrying out arc welding, comprising an opaque shell, a vision window in said opaque shell, a movable frame having at least one obscured glass arranged in said vision window for displacement between a position of inactivity and a position of activity in which it obscures said vision window, a housing separate from said opaque shell, an actuation means arranged within said housing, a sheath connected at one end to said opaque shell and at the other end to said housing, and a flexible cable connected at one end to said movable frame and at the other end to said actuation means, said sheath and flexible cable forming a transmission means for displacing said movable frame under action of said actuation means;

the improvement that said actuation means comprises an electromagnet having an electric winding adapted to be connected to the electric circuit of an arc welding apparatus, and an anchor cooperable with said electromagnet, and bayonet joint means inserted between said sheath and said housing as well as between said flexible cable and said anchor, whereby said housing with the actuation means can be connected and disconnected by a single operation to and from said transmission means and opaque shell.

2. A welding mask as set forth in claim 1, wherein said bayonet joint means comprise a first bayonet joint between said flexible cable and said anchor, a ring nut coupled with said sheath, a neck on said housing, said neck having an inner bore larger than said first bayonet joint, and a second bayonet joint between said ring nut and neck, the coupling travel of said second bayonet joint being longer than the coupling travel of said first bayonet joint.

3. A welding mask as set forth in claim 1, further comprising a preloaded spring device interposed between said flexible cable and said movable frame.

4. A welding mask as set forth in claim 1, further comprising a preloaded spring device interposed between said flexible cable and said actuation means.

* * * * *